(12) United States Patent
Nallakrishnan et al.

(10) Patent No.: US 6,547,802 B1
(45) Date of Patent: Apr. 15, 2003

(54) SURGICAL BLADE

(76) Inventors: Ravi Nallakrishnan, 26 Plaza Dr., Westmont, IL (US) 60559; Lee T. Nordan, 6183 Paseo del Norte, Carlsbad, CA (US) 92009

(*) Notice: Subject to any disclaimer, the term of this patent is extended or adjusted under 35 U.S.C. 154(b) by 0 days.

(21) Appl. No.: 09/375,660

(22) Filed: Aug. 21, 2001

(51) Int. Cl.⁷ .................................................. A61F 5/00
(52) U.S. Cl. ...................................... 606/166; 606/167
(58) Field of Search ................................ 606/166, 167, 606/168, 170, 172, 180, 181

(56) References Cited

U.S. PATENT DOCUMENTS

| | | | | |
|---|---|---|---|---|
| 4,163,317 A | * | 8/1979 | Levanti | 30/123.7 |
| 4,319,564 A | * | 3/1982 | Karickhoff | 600/587 |
| 4,552,146 A | * | 11/1985 | Jensen et al. | 606/166 |
| 5,203,865 A | * | 4/1993 | Siepser | 606/166 |
| 5,217,476 A | * | 6/1993 | Wishinsky | 606/167 |
| 5,370,652 A | * | 12/1994 | Kellan | 606/166 |
| 5,713,915 A | * | 2/1998 | Van Heugten et al. | 606/167 |
| 6,139,559 A | * | 10/2000 | Nordan et al. | 606/166 |

* cited by examiner

Primary Examiner—Kevin T. Truong
Assistant Examiner—Victor Nguyen
(74) Attorney, Agent, or Firm—Jerry A. Schulman

(57) ABSTRACT

A surgical blade for use in ophthalmic surgery has a multi-faceted distal end with cutting edges which meet at an angle greater than 90° and preferably 140°, resulting in a blade with a relatively large surface area. An anterior shoulder is positioned intermediate the distal and proximal ends of the blade to direct the blade to dimple down when the blade has been inserted into the cornea a sufficient distance to bring the shoulder into contact with the corneal tissue, allowing the surgeon to make a linear entry into the anterior chamber resulting in a reproducible, leak-free incision by using a straight-in hand motion. The blade is rounded at certain of its lateral edges to avoid snagging the incision when the blade is passed through the cornea.

24 Claims, 4 Drawing Sheets

SURGICAL BLADE

BACKGROUND OF THE INVENTION

1. Field of the Invention

The present invention relates generally to surgical knife blades and in particular to blades used in ophthalmological surgical procedures such as clear corneal incisions.

2. Description of the Prior Art

Ophthalmic surgeons work within a very small operating field upon organs whose tissues are complex and delicate. Cuts made during surgery must be precise as to length, direction and depth, requiring surgical knives of unsurpassed sharpness and maneuverability and with configurations particularly suited to operating upon selected portions of the eye.

It has become well-known to design blades for ophthalmological knives to perform specific cuts used in certain types of eye surgery. One type of ocular surgery used to correct cataracts is referred to as clear corneal cataract surgery, discussed in an article entitled "Beveled blades have simplified clear corneal technique" by William F. Maloney, M.D., appearing in the Sep. 15, 1997 issue of *Ocular Surgery News* in which clear corneal surgery is generally described as the use of a beveled diamond blade to make a three-step incision to form a path through the cornea and into the anterior chamber of the eye.

As mentioned by Dr. Maloney, examples of known beveled blades are the Rhein 3-D trapezoid blade manufactured by Rhein Medical, Inc. of Tampa Fla., the Accutome beveled diamond manufactured by Accutome of Malvern, Pa., the Storz multi-beveled diamond manufactured by Storz of St. Louis, Mo. and the pyramid diamond manufactured by KMI of Paoli, Pa. All feature a blade profile having a posterior surface formed generally as an elongated "home plate" type of pentagon with a leading, sharply V-shaped pointed tip, an anterior surface shaped generally to correspond to the posterior surface and a series of bevels extending from the anterior surface to the posterior surface.

The Pathfinder® blade sold by American Surgical Instruments Corporation of Westmont, Ill. features a tip characterized by cutting edges which meet at a significantly greater angle than those of the blades described above.

Cutting edges are formed where two bevels intersect, or where a bevel intersects an anterior or posterior surface, most typically resulting in a pair of cutting edges diverging from a leading point or distal end of the blade along the legs of a V to intersect with a pair of lateral cutting edges formed along that portion of the blade extending from the distal end rearward toward the proximal end which is adapted to be gripped by a knife or blade holder. Certain known blade configurations feature lateral cutting edges that are substantially parallel while other configurations feature lateral cutting edges that diverge along the distal-to-proximal direction, allowing the width of the incision to be determined by the distance to which the blade is inserted through the corneal membranes, with the incision being widened as the blade is inserted.

Removing a damaged or diseased lens and replacing it with an artificial intraocular lens calls for the surgeon to make incisions in the cornea or the sclera through which fragments of the old lens are removed and through which the new lens is inserted. Techniques are now used to fold the new lens prior to insertion and to allow it to unfold once it is in place, requiring a relatively small, straight incision which heals quickly and, if properly made, limits or eliminates fluid leakage from the eye without requiring suturing or hydration.

The cornea is made up of several tissue layers through which an incision must be made to reach the anterior chamber of the eye, principally the anterior epithelium, Bowman's membrane and Descemet's membrane. A description of the problems inherent in making such incisions and the techniques presently required is found in U.S. Pat. No. 5,713,915 (Van Heugten, et al.). According to Van Heugten, et al., because the cornea is spherical in shape, such cuts tend to produce non-linear incision lines unless they are made at a 90° angle to the surface being cut. One presently known technique for making linear, water-tight incisions is described as "dimpling down" which requires a surgeon to attempt to flatten the cornea, or "dimple down" as soon as the tip of the surgical blade reaches Descemet's membrane in order to create a substantially linear, perpendicular incision through the membrane. According to Van Heugten, et al., dimpling down requires the surgeon to lift the back of the blade up to point the tip of the blade down which can cause distortion in the tunnel formed by the cut. Lifting the back of the blade also increases the angle of the cut, making it less tangential to the circumferential arc of the cornea, affecting the water-tight integrity of the unsutured incision. To compensate, the surgeon must hydrate the corners of the incision.

U.S. Pat. No. 5,713,915 (Van Heugten, et al.) teaches and describes a surgical knife blade for use in ophthalmological surgery characterized by sharply pointed tip and a non-symmetrical lateral profile, with cutting edges formed by the intersection of differently-sized anterior and posterior bevels to position the cutting edges closer to the anterior surface than the posterior surface. Van Heugten, et al. state that curved incisions result most directly from the use of blades that are typically symmetrical when the anterior surface is compared to the posterior surface. Also claimed in Van Heugten, et al. are side edges formed by anterior and posterior bevels, with the side edges meeting the cutting edges at a shoulder and with the side edges and the cutting edges being equal at the shoulder.

Other prior art blades used to incise the cornea characteristically have sharply pointed tips and fall generally into two categories: symmetrical blades with cutting edges formed by bevels and positioned substantially midway between anterior and posterior blade surfaces, and blades with edges formed by a bevel formed on one blade surface intersecting the plane of the other surface.

U.S. Pat. No. 5,676,679 (Simon et al) teaches and describes an apparatus for implanting an artificial meshwork in glaucoma surgery featuring a surgical blade having a point set at an acute angle and having a pair of anterior bevels extending along the edges forming the point and from a top surface to a flat bottom surface. The blade of Simon et al. has been modified to form a "hook" along the upper surface within which a mesh implant may be retained for positioning within the eye chamber.

U.S. Pat. No. 4,688,570 (Kramer, et al.) teaches and describes an ophthalmological surgical instrument used to guide a knife in cutting radial keratomatic incisions in the cornea. The knives shown in Kramer, et al. are of the type having anterior and posterior bevels intersecting midway through the blade's thickness to form the cutting edges.

U.S. Pat. No. 5,201,747 (Mastel) teaches and describes an ophthalmological surgical instrument having a triple edge tip using opposed bevels to form a symmetrical blade.

U.S. Pat. No. 5,217,476 (Wishinsky) teaches and describes a surgical knife blade and method of performing cataract surgery utilizing a surgical knife blade which is symmetrical and beveled to form a centrally-positioned cutting edge.

U.S. Pat. No. 5,224,950 (Prywes) teaches and describes a color calibrated multi-function scalpel blade for intraocular and other surgery and associated methods of use showing symmetrical cutting edges and a color-coded blade to indicate how deeply the blade has been inserted.

U.S. Pat. No. 5,376,099 (Ellis, et al.) teaches and describes an undercut diamond surgical blade and method of using the same having a non-symmetrical pointed cutting tip, the cutting edges of which are centered between the two surfaces of the blade and are formed by bevels on the blade sides.

U.S. Pat. Nos. 5,203,865 and 5,098,438 (Siepser) teach and describe surgical knives for use in ophthalmic surgery and procedures for intraocular surgery in which a variety of surgical knives are described of the type having parallel surfaces and cutting edges formed by the intersection of bevels extending from one face to the other.

U.S. Pat. No. 5,370,652 (Kellan) teaches and describes a surgical knife blade for making sutureless incisions in the eye and methods therefor which discloses several blade configurations with cutting edges formed by the intersection of a posterior bevel with the anterior surface of the blade.

U.S. Pat. No. 5,405,355 (Peyman, et al.) teaches and describes a method of radial keratotomy employing a vibrating cutting blade in which a triangular blade with cutting edges formed by blade face bevels is disclosed.

U.S. Pat. No. 5,222,967 (Casebeer) teaches and describes a keratorefractive diamond blade and surgical method illustrating a blade with a cutting edge formed by intersecting blade bevels.

U.S. Pat. No. 5,336,235 (Myers) teaches and describes a keratome having a curved, pointed blade with a cutting edge formed by the intersection of a bevel on the upper, curved surface with the lower, curved surface.

These references generally exemplify surgical blades having "pointy" blade tips, that is, blades whose cutting edges meet at an acute angle. It is believed that this design creates problems when making the type of incision required for clear corneal surgery. In particular, the available surface area of the blade available to support the tissue during cutting is limited when compared to the surface area of a blade whose lead cutting edges meet at a larger angle. Adopting the cutting profile of the present invention thus teaches away from the present art because such a profile would seem to require significantly more force to start a cut, a factor that must be balanced against the advantage of having a larger surface area to support the tissues being incised. However, this has not been the case. Blades made in accordance with the teachings of the present invention have been successfully used in clear corneal surgery.

The American Surgical Instruments Corporation Pathfinder® blade has leading cutting edges that meet at a relatively large angle and has a stepped configuration with an upper shoulder that automatically directs the blade down to make a linear incision, a configuration that performs its function well. The present invention seeks to match that performance with a thinner blade having a simple configuration intended to enhance further the automatic dimple down effect. One way to achieve this result (and to produce a blade which is easy to manufacture) is to create a blade configuration with a flat, planar bottom manufactured without undercut bevels to form cutting edges.

It is an object of the clear corneal surgical technique to make an incision that seals itself and does not require sutures to prevent leakage of fluid from the anterior chamber of the eye. It has been found that a single lateral incision which extends partially through the cornea and then changes to a direction more approximating a line perpendicular to Descemet's membrane creates a path or tunnel through the corneal tissue which effectively seals itself and does not leak if the entry into the anterior chamber is linear. The first segment of this incision through the outer corneal tissue is identified as the inner corneal valve, while the second, stepped portion of the incision is called the anterior chamber entry.

It is believed that one of the keys to making such an incision self-sealing is to maximize the surface area of the cut, that is, the surface area of the "roof" and "floor" of the tunnel. Another factor is the ability to keep the edges of the incision straight, not allowing them to tear or sag down and to make the cross-section of the anterior chamber entry as linear as possible.

Another problem is thought to result when the blade is withdrawn after it has pierced Descemet's membrane. There are times when the edges of the incision are torn, presumably when the edges snag on a portion of the blade as it is withdrawn or when the surgeon is required to abruptly change the angle of the blade to dimple down. Such tears cause leaks.

It is also desirable to have a blade configuration which allows the surgeon to make accurate, reproducibly self-sealing incisions without having to estimate the depth of cut and without relying upon the need to change hand positions during the incision or to estimate the angle to which the blade must be brought to effectively dimple down and complete the incision.

Accordingly, it is an object of the present invention to provide a blade to be used for ophthalmological surgical procedures that will create a reproducibly self-sealing incision when used to penetrate the corneal tissue, eliminating the need for sutures.

It is also an object of the present invention to provide such blades in configurations which maximize the surface area of the incision to enhance the self-sealing action.

It is a further object to provide such blades in configurations which support the incision as it is being made to limit the tendency of the incision edges to sag or tear.

Another object is to provide such blades in configurations which automatically create a dimpling down action at a reproducible depth of cut through the corneal tissue without requiring the surgeon to change hand positions to select an entry angle.

Still another object of the present invention is to provide such blades in configurations which reduce the tendency of the blade to snag on the edges of the incision when the blade is being withdrawn.

Another object is to provide such blades with flat, planar bottoms to simplify the manufacturing process and to allow the blade to be made with a thinner lateral profile.

Yet another object of the present invention is to provide such blades in forms which are thinner yet retain all the desirable characteristics set forth above.

It is clear from the foregoing that there is a demonstrated need for a surgical blade for use in ophthalmological surgical procedures which is capable of reproducibly creating a leak-proof corneal incision through which other surgical procedures may be carried out without requiring the surgeon to make adjustments in hand position or to determine visually when or to what extent the angle of cut should be changed.

SUMMARY OF THE INVENTION

A diamond surgical blade for clear corneal surgery has a lead cutting surface characterized by a pair of anterior point bevels, a pair of posterior point bevels and a pair of anterior side bevels, with distal cutting edges formed by the intersection of the distal posterior point bevels with a flat, posterior surface of the blade, with the bevels meeting each other at an angle of about 140° as measured at the posterior surface. An elevated shoulder is formed on the anterior surface intermediate the distal and proximal ends of the blade, preferably at a distance of about 1.5 mm from the distal end of the blade and extending to a distance of about 0.05 mm above the distal portion of the anterior surface.

When the blade is inserted into the cornea to a distance of about 1.5 mm, the shoulder comes into contact with the corneal tissue and automatically directs the blade in a dimple down motion to pierce Descemet's membrane in a linear fashion. This allows the surgeon to make the incision using a linear or straight-in motion without changing the angle of the blade to dimple down. The shape of the blade allows a thinner profile yet produces a cut or tunnel having a larger surface area than that made by more pointed prior art blades and the sharpened edges resist the tendency to change the shape of the incision as the blade is withdrawn. Rounded blade shoulders formed at the lateral ends of the distal cutting edges tend to prevent the blade from tearing the edges of the incision when the withdrawn. Use of the anterior, posterior and side bevels allows the blade to be inserted into the tissue without requiring an undue amount of force even though the blade point angle is relatively large.

While the following describes a preferred embodiment or embodiments of the present invention, it is to be understood that such descriptions are made by way of example only and are not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed.

BRIEF DESCRIPTION OF THE DRAWINGS

These and further aspects of the present invention will become more apparent upon consideration of the following drawings, in which like numerals indicate like parts, and in which.

DETAILED DESCRIPTION OF THE DRAWINGS

Figure 1:
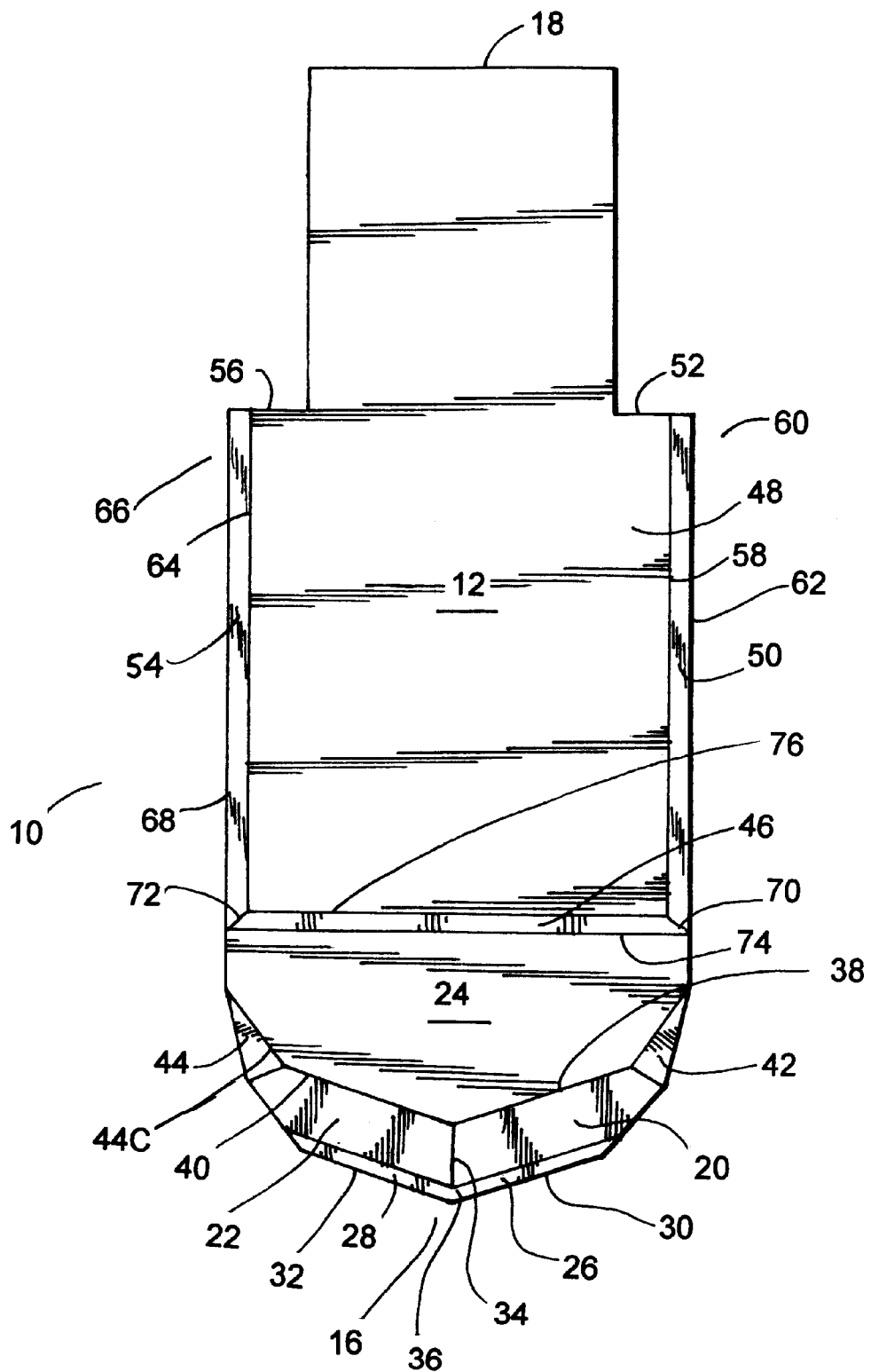
FIG. 1 is a top plan view of the surgical blade of the present invention.

Referring now to FIG. 1, the numeral 10 indicates generally a surgical blade embodying the present invention. Blade 10 is particularly adapted for use in ophthalmological surgery and, more particularly, for use in making incisions through the cornea of the eye. While it is possible to manufacture blade 10 from a variety of materials such as, for example, steel, glass, ceramics, precious or semi-precious stones and artificial stones, the blade material preferably comprises diamond and is so illustrated in the accompanying drawings.

Figure 3:
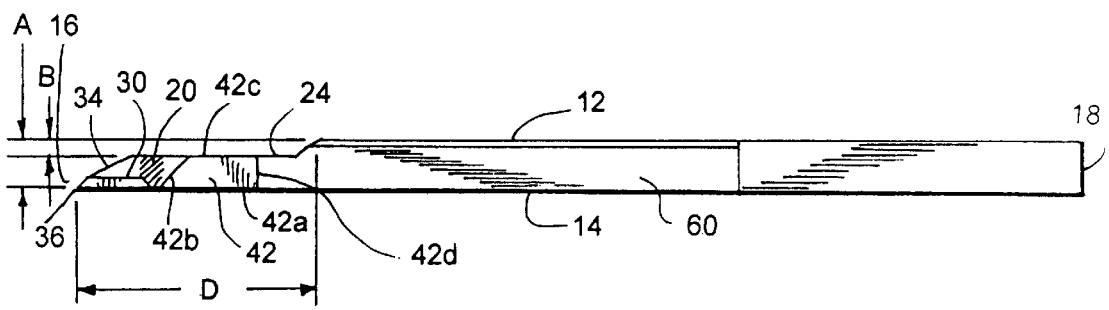
FIG. 3 is a lateral plan view of the blade of FIG. 1.

As seen in FIGS. 1 and 3, blade 10 has a stepped anterior surface 12 and a flat posterior surface 14. Blade 10 is also configured with a distal piercing end or point 16 and a proximal or handle end 18 which is secured to a handle, it being understood that the handle may be in the form of a number of known blade holders presently in use in connection with ophthalmological surgery. While the blade is can be made in varying in sizes and configurations, in the embodiment herein shown blade 10 is approximately 2.5 mm in width and extends a distance of 6.5 mm from the distal end 16 to proximal end 18 at the point where proximal end 18 is secured to the handle.

Figure 2:
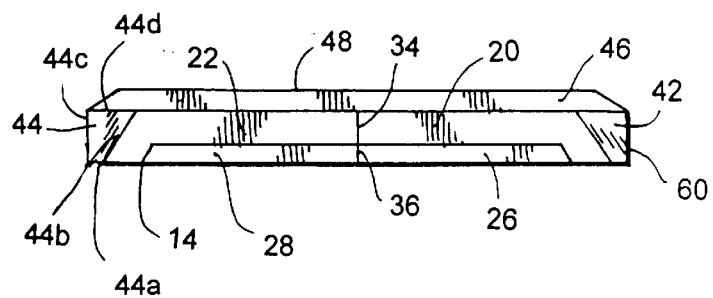
FIG. 2 is a front plan view of the blade of FIG. 1.

In FIG. 1, blade 10 is shown having a first upper anterior bevel 20 and a second upper anterior bevel 22, with first bevel 20 extending to a first lower anterior bevel 26 and second bevel 22 extending to a second lower anterior bevel 28. Bevels 26 and 28 extend to posterior surface 14. The intersection of first lower bevel 26 and posterior surface 14 forms a first cutting edge 30 while the intersection of second lower bevel 28 and posterior surface 14 forms a second cutting edge 32. The intersection of bevels 26 and 28 also forms a distal end or point 16. In the embodiment herein shown, bevels 26 and 28 are angled such that cutting edges 28 and 30 meet at ridge 36 at an angle of approximately 140°. FIG. 2 also shows that bevels 20 and 22 intersect to form upper distal ridge 34 while lower bevels 26 and 28 intersect to form a lower distal ridge 36.

As seen in FIG. 1, bevel 20 intersects with facet 24 to form a first facet edge 38 and a second facet edge 40.

Referring to FIG. 1, a first anterior side bevel 42 is shown adjacent first anterior point bevel 20 and a second anterior side bevel 44 is shown adjacent second anterior point bevel 22.

As seen in FIG. 3, side bevel 42 is defined by lower edge segment 42a, lead edge 42b, upper edge segment 42c and trailing edge segment 42d.

As seen in FIGS. 1 and 2, second side bevel 44 is bounded by lower edge segment 44a, lead edge segment 44b, upper edge segment 44c and trailing edge segment 44d.

As seen in FIG. 1 a transverse bevel 46 is shown extending between anterior facet 24 and an upper shoulder 48 in a "step" configuration. A first lateral bevel 50 is formed depending from shoulder 48, extending toward handle end 18 and terminating at rear edge 52. A corresponding second lateral bevel 54 extends parallel to bevel 50 and terminates at rear edge 56. Bevel 50's intersection with shoulder 48 forms a first upper edge 58 and its intersection with sidewall 60 forms a first medial edge 62. Similarly, bevel 54's intersection with shoulder 48 forms a second upper edge 64 and its intersection with sidewall 66 forms a second medial edge 68.

Transverse bevel 46 intersects first lateral bevel 50 to form first upper shoulder edge 70 and intersects bevel 54 to form a second upper shoulder edge 72. In addition, a lower transverse line 74 is formed to mark the intersection of anterior facet 24 and transverse bevel 46, while the intersection of transverse bevel 46 and upper shoulder 48 forms an upper transverse edge 76.

Figures 4, 5:
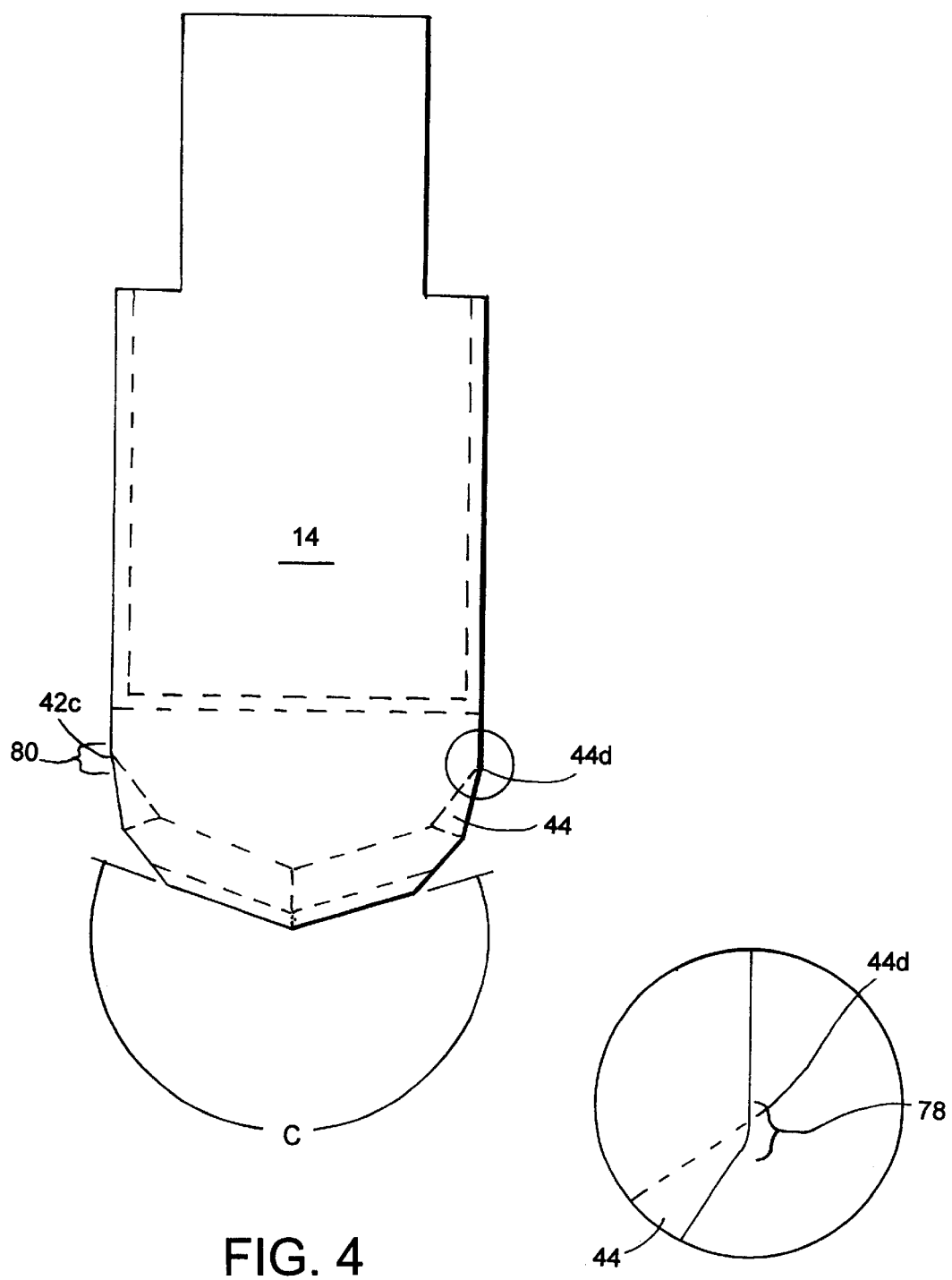
FIG. 4 is a bottom plan view of the blade of FIG. 1.
FIG. 5 is an enlargement of detail E in FIG. 4.

FIG. 4 is a bottom view of the blade of FIG. 1, demonstrating that posterior surface 14 is planar with no undercuts or posterior bevels. This maximizes the surface area of blade 10 which forms the floor of the incision to be described in more detail below.

FIG. 5 is an enlargement of detail E shown in FIG. 4, showing that at trailing edge segment 44d blade 10 is preferably formed as a rounded segment 78. Correspondingly, at trailing edge segment 42d blade 10 is similarly formed as a rounded segment 80, as indicated in FIG. 4.

Figure 7:
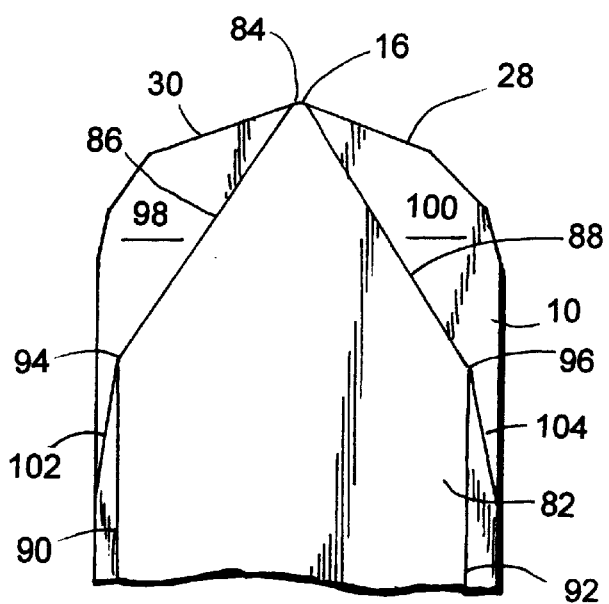
FIG. 7 is a plan view comparison of the surface area of the blade of FIG. 1 and certain prior art clear corneal blade configurations.

FIG. 7 is a comparison of the profile of blade 10 with the profiles of the blades shown in Van Heugten, et al., illustrating the relatively larger surface area of blade 10.

Figure 6:
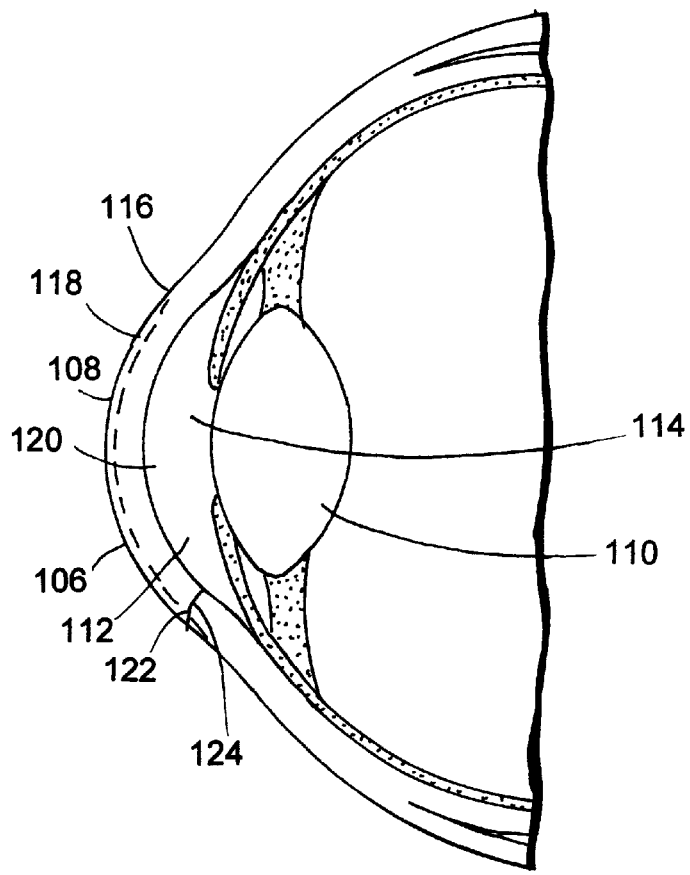
FIG. 6 is a partial lateral sectional view of the human eye.

Blade 82 corresponds generally to the profile of the blade shown in FIG. 6 of Van Heugten, et al., having a point 84 (coinciding with point 16 of blade 10), a pair of diverging anterior cutting edges 86, 88, a pair of lateral cutting edges 90, 92, with cutting edges 86 and 90 meeting at shoulder 94 and cutting edges 88, 92 meeting at a shoulder 96. The areas 98, 100 of blade 10 demonstrate the increased surface area of blade 10 as compared to blade 82.

A second blade configuration is shown in FIG. 11 of Van Heugten, et al., having a pair of lateral cutting edges 102, 104 diverging from, respectively, shoulders 94, 96. Even with the diverging lateral edges, FIG. 7 clearly illustrates that blade 10 presents a greater surface area than either of the two blade configurations discussed.

Van Heugten, et al. has been selected as representative of similar surgical blades characterized by cutting edges meeting at acute angles and diverging distally. See, for example, FIG. 2 of Van Heugten, et al., illustrating another prior art blade. The comparison of blade profiles is made without considering the other characteristics of the compared blades, such as the presence and sizes of bevels, shoulders and the like. It should be noted that the examples of prior art blades described herein all have cutting edges meeting at acute angles.

Use of the present invention may now be described with particular reference to FIG. 6 in which a lateral view of an eye 106 is shown with a cornea 108, a lens 110, an anterior chamber 112 and an iris 114. Principal components of the cornea are the anterior epithelium 116, Bowman's membrane 118 and Descemet's membrane 120. In performing a clear corneal transplant, the lens 110, which may be damaged or diseased, must be removed and a new, artificial lens inserted in its place. To do so, an incision is formed laterally through cornea 108, lens 110 is broken into fragments or emulsified, and the fragments are aspirated through the incision. Thereafter, an artificial lens is inserted through the incision by folding the lens in half and holding the lens in a forceps. After the forceps have been inserted into the incision, the lens is allowed to unfold and is positioned properly within anterior chamber 112.

Critical to the success of such an operation is the making of a self-sealing incision to prevent leakage or loss of fluid from anterior chamber 112. It has been found that the creation of a stepped incision will cause the incision to close upon itself when the operation is complete and will form a watertight seal without requiring the use of sutures. This greatly shortens the healing process as well as the time during which the operation takes place.

As seen in FIG. 5, the incision is typically made laterally and, in prior art procedures, a pointed diamond blade is inserted laterally to form the first incision part, or inner corneal valve 122. At some point prior to the cutting of Descemet's membrane 120, the blade would then be angled or "dimpled" down to cut through the remaining corneal tissue along entry 124 and to align the blade 10 at right angles to Descemet's membrane 120 to enter anterior chamber 112. Typically, the thickness of the cornea is about 2.0 mm. Selection of distance D to be 1.5 mm is intended to allow blade 10 to be inserted into the cornea 108 and to have the corneal tissue contact transverse bevel 46 and, thereafter, upper shoulder 48 to create an inner corneal valve 122 of about 1.5 mm in length prior to piercing Descemet's membrane 120. Contact of tissue with upper shoulder 48 forces blade 10 downward to automatically dimple down prior to distal end 16 contacting Descemet's membrane 120 to make a linear entry into the anterior chamber. Because of the geometry of blade 10, the dimpling down effect is obtained without requiring the surgeon to change hand positions or estimate the proper angle required to make a perpendicular entry. In addition, the surgeon is not required to gauge or estimate how far blade 10 has been inserted into cornea 108 before the dimpling down must occur.

After blade 10 has been inserted to completely cut through cornea 108, it is then withdrawn and if linearity is maintained a good seal will result. The remaining surgical procedures then may be performed to remove and replace lens 110. Rounded edges 78, 80 allow blade 10 to be withdrawn without snagging cornea 108 to tear inner corneal valve 122 or entry 124.

As can be seen in the prior art references discussed above, a typical diamond blade used for this type of surgery (such as that shown in Van Heugten et al.) is sharply pointed, that is, the angle between the distal cutting edges is an acute angle and the cutting edges thereafter diverge, eventually reaching the width of cut desired. Thus, the cut is being progressively enlarged as the blade pierces the cornea. When the blade is first inserted, there is a minimum amount of surface area available to support the tissues during the cutting process: it is only as the divergent part of the blade enters the incision, more surface area is made available to support the tissue and guide the blade during the cut. In addition, when a pointed prior art blade pierces into anterior chamber 112, the incision will not extend the fullest width of the blade unless the blade is inserted to bring its widest part into anterior chamber 112.

The present invention, on the other hand, adopts a broader lead cutting edge by having first and second cutting edges 28 and 30 meet at an angle C of approximately 140°. It is believed that the tearing or distortion at the edges of the incision which are suspected to cause leakage are avoided by the cutting surface presented to cornea 108 which supports the corneal tissue over a much larger surface area throughout the incision process and presents an incision having a relatively larger surface area than that made with prior art blades. As blade 10 pierces through to anterior chamber 112, the cut at Descemet's membrane 120 is as wide as the full width of blade 10.

While the foregoing examples are presented as preferred embodiments, it should be readily apparent that blades of differing dimensions and configurations may be supplied in instances where the corneal thickness differs from the norm and where it is necessary or desirable to form a wider or narrower incision.

What is claimed is:

1. A surgical knife blade comprising:
   an elongated body having a proximal end, a distal end, opposed anterior and posterior surfaces, and first and second opposed longitudinal sides extending between said proximal end and said distal end;
   a compound faceted cutting face positioned at said distal end and extending from said first longitudinal side to said second longitudinal side, said cutting face having first and second anterior bevels formed at said distal end;

first and second cutting edges located at said distal end, said first and second cutting edges being formed by the intersection of said first and second anterior bevels with said posterior surface, said intersection of said first and second anterior bevels with said posterior surface positioning said first and second cutting edges to be substantially coplanar with said posterior surface at said distal end;

first and second side facets, said first side facet contiguous with said first anterior bevel and extending from said first anterior bevel to said first longitudinal side, said second side facet contiguous with said second anterior bevel and extending from said second anterior bevel to said second longitudinal side, said first and second cutting edges being disposed at an angle greater than 90° with respect to each other as measured in the plane of said posterior surface.

2. The apparatus as recited in claim 1 wherein said blade further comprises a top shoulder formed on and extending a distance above said anterior surface intermediate said distal and proximal ends.

3. The apparatus as recited in claim 2 wherein said angle is 140°.

4. The apparatus as recited in claim 2 wherein said first cutting edge has a first rounded corner formed thereon proximate the distal end of said first longitudinal side, and said second cutting edge has a second rounded corner formed thereon proximate the distal end of said second longitudinal side.

5. The apparatus as recited in claim 2 wherein said distance above said anterior surface is 0.1 mm.

6. The apparatus as recited in claim 2 wherein said top shoulder is formed on said anterior surface between 1.0 to 2.0 mm from said distal end.

7. The apparatus as recited in claim 6 wherein said top shoulder is formed on said anterior surface 1.75 mm from said distal end.

8. The apparatus as recited in claim 2 further comprising a handle attached to the proximal end of said blade.

9. The apparatus as recited in claim 2 wherein said blade is fashioned from diamond material.

10. The combination as recited in claim 1 wherein said first bevel includes a first upper facet and a first lower facet, and said second bevel includes a second upper facet and a second lower facet, each said upper facet extending from said anterior surface to its corresponding lower facet and each said lower facet extending from its corresponding upper facet to intersect said posterior surface to form said cutting edges.

11. The combination as recited in claim 10 wherein each said upper and lower facets intersect to form a lower edge and said each said upper facet intersects with said anterior surface to form an upper edge, said upper edges being longer in length than said lower edges.

12. The combination as recited in claim 10 wherein said first upper facet intersects said first side facet and said second upper facet intersects said second side facet.

13. A surgical knife blade comprising:

an elongated body having a proximal end, a distal end, opposed anterior and posterior surfaces, and first and second opposed longitudinal sides extending between said proximal end and said distal end;

a compound faceted cutting face positioned at said distal end and extending from said first lateral side to said second lateral side, said cutting face having first and second anterior bevels formed at said distal end;

first and second cutting edges located at said distal end, said first and second cutting edges being formed by the intersection of said first and second anterior bevels with said posterior surface, said intersection of said first and second anterior bevels with said posterior surface positioning said first and second cutting edges to be substantially coplanar with said posterior surface at said distal end;

first and second side facets, said first side facet contiguous with said first anterior bevel and extending from said first anterior bevel to said first longitudinal side, said second side facet contiguous with said second anterior bevel and extending from said second anterior bevel to said second longitudinal side, said first and second cutting edges being disposed at an angle greater than 90° with respect to each other as measured in the plane of said posterior surface; and a top shoulder formed on and extending a distance above said anterior surface intermediate said distal and proximal ends.

14. The apparatus as recited in claim 13 wherein said first and second cutting edges are disposed at an angle greater than 90° with respect to each other as measured in the plane of said posterior surface.

15. The apparatus as recited in claim 14 wherein said angle is 140°.

16. The apparatus as recited in claim 13 wherein said first cutting edge has a first rounded corner formed thereon proximate the distal end of said first longitudinal side, and said second cutting edge has a second rounded corner formed thereon proximate the distal end of said second longitudinal side.

17. The apparatus as recited in claim 13 wherein said distance above said anterior surface is 0.1 mm.

18. The apparatus as recited in claim 13 wherein said top shoulder is formed on said anterior surface between 1.0 to 2.0 mm from said distal end.

19. The apparatus as recited in claim 18 wherein said top shoulder is formed on said anterior surface 1.75 mm from said distal end.

20. The apparatus as recited in claim 13 further comprising a handle attached to the proximal end of said blade.

21. The apparatus as recited in claim 13 wherein said blade is fashioned from diamond material.

22. The combination as recited in claim 13 wherein said first bevel includes a first upper facet and a first lower facet, and said second bevel includes a second upper facet and a second lower facet, each said upper facet extending from said anterior surface to its corresponding lower facet and each said lower facet extending from its corresponding upper facet to intersect said posterior surface to form said cutting edges.

23. The combination as recited in claim 22 wherein each said upper and lower facets intersect to form a lower edge and said each said upper facet intersects with said anterior surface to form an upper edge, said upper edges being longer in length than said lower edges.

24. The combination as recited in claim 22 wherein said first upper facet intersects said first side facet and said second upper facet intersects said second side facet.

* * * * *